United States Patent [19]

Beilman

[11] 4,065,957

[45] Jan. 3, 1978

[54] FLUID SPEED INDICATING APPARATUS AND DENSITOMETER

[75] Inventor: John L. Beilman, Lancaster, N.Y.

[73] Assignee: Calspan Corporation, Buffalo, N.Y.

[21] Appl. No.: 742,142

[22] Filed: Nov. 15, 1976

[51] Int. Cl.² .......................... G01F 1/50; G01N 9/34
[52] U.S. Cl. .......................................... 73/30; 73/182; 73/189
[58] Field of Search ................. 73/30, 32 R, 181, 182, 73/189, 205 D

[56] References Cited

U.S. PATENT DOCUMENTS 3,400,584    9/1968    Beilman ................................. 73/182

FOREIGN PATENT DOCUMENTS 387,404    12/1923    Germany ................................. 73/30
236,844    11/1969    U.S.S.R. ................................. 73/30

Primary Examiner—James J. Gill
Attorney, Agent, or Firm—Allen J. Jaffe; David J. Zobkiw

[57] ABSTRACT

Fluid density is measured in a fluid speed indicating apparatus by using a pair of rotor arms having a pair of asymetrically located venturis or equivalent venturis. A steady state pressure difference will be produced between the two pressure locations and will be a function of the rotational velocity and fluid density. Since the rotational velocity is a known constant, the fluid density can be derived directly from the steady state pressure difference.

5 Claims, 6 Drawing Figures

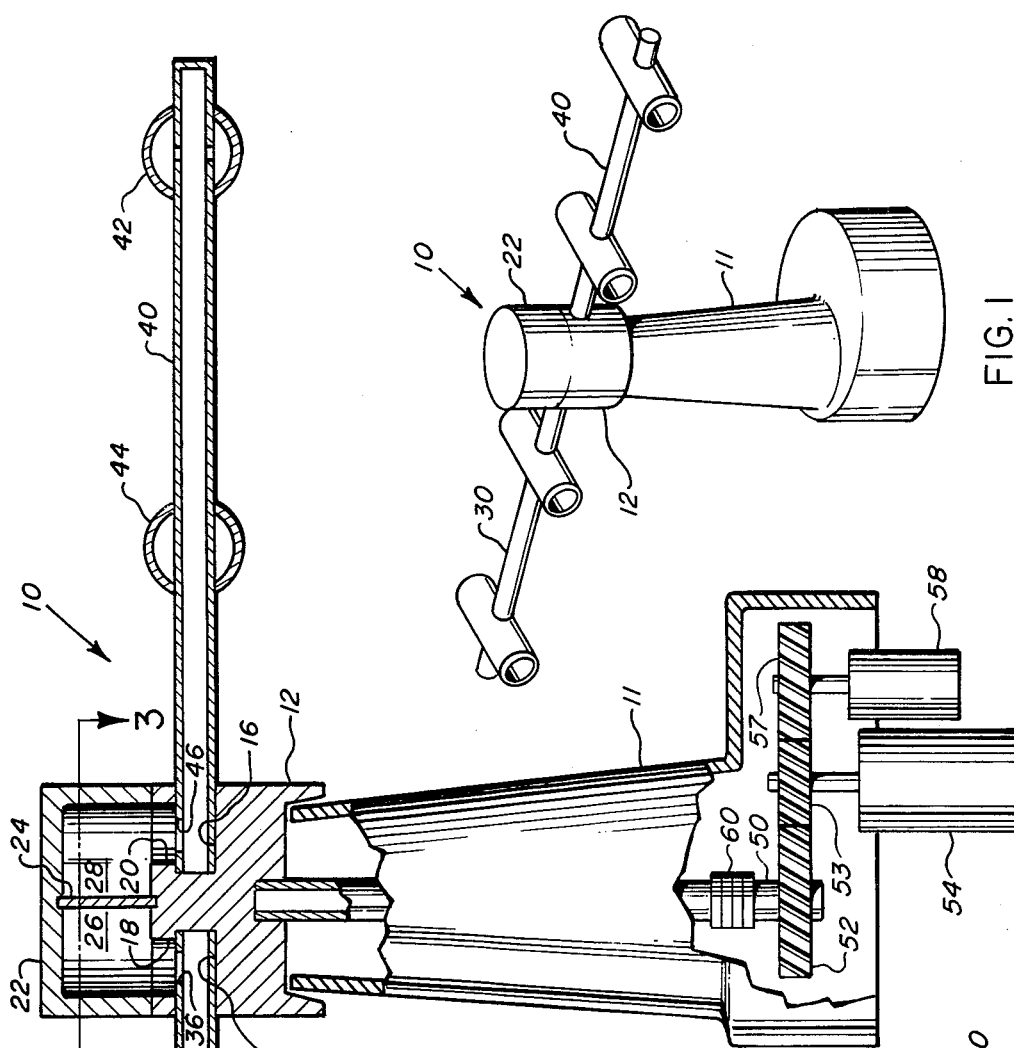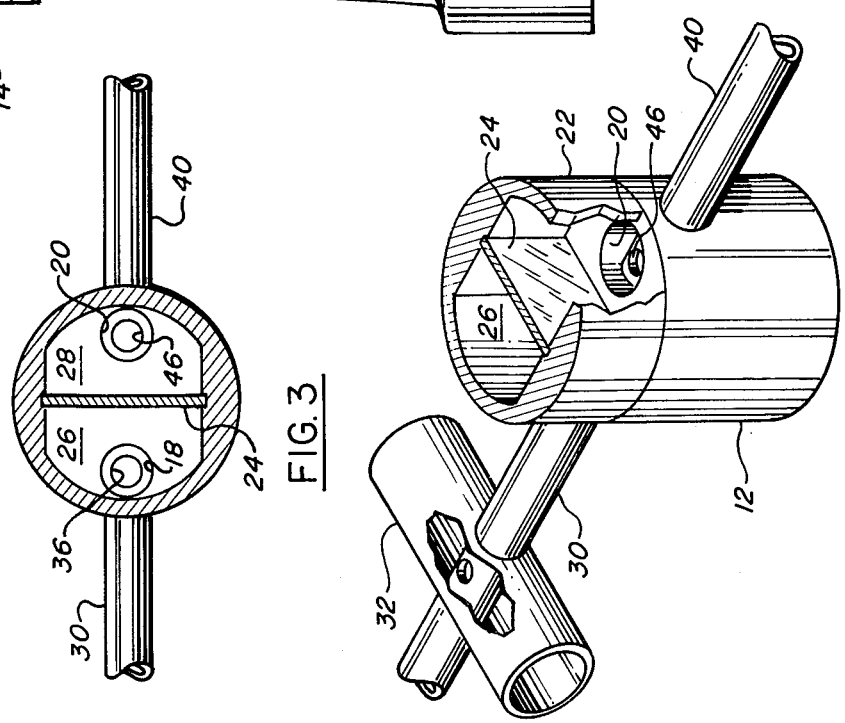

FLUID SPEED INDICATING APPARATUS AND DENSITOMETER

The present invention relates to airspeed indicators, and more particularly to airspeed indicators that are sensitive to very low airspeeds and incorporate a densitometer.

Airspeed indicators are known which are designed to measure the low airspeeds encountered in helicopter or VTOL flights. These indicators comprise one or more rotating pitot tubes, wherein the amplitude of the cyclic variations in pressure sensed by the tube or tubes, as they move into the direction of flight and away therefrom, is directly proportional to the forward velocity or airspeed of the aircraft. To develop higher pressure differentials for greater sensitivity at low airspeeds, these types of indicators utilize independent motor means to rotate the tubes. In this manner, the pressures sensed by the tubes are much higher than those that would be developed only by the low airspeed.

Earlier devices were unable to measure airspeeds below a minimum threshold value and the reason is though to be due to a radial flow or whirl that is generated by the instrument itself. The earlier used instrument basically comprises a rotating arm having a pitot tube at the end thereof. The rotating arm generates a flow from above and below the arm center and radially outward along the length of the arm, much like the action of a centrifugal pump. At very low airspeeds, this flow enveloping the pitot tube prevents the tube from sensing the pressures which are generated by the forward speed of the aircraft. At higher speeds this induced flow has not interfered with operation of the instrument or measurement of velocity.

These difficulties in obtaining low speed measurements were overcome by the devices disclosed in my prior U.S. Pat. Nos. 3,373,605, 3,400,584 and 3,726,139. One of the difficulties of the fluid/air speed indicating devices disclosed in my earlier U.S. patents is the necessity for measuring static pressure and free air temperature in order to provide density compensation for the airspeed measurement. In addition to the physical problems involved in obtaining an accurate measurement of static pressure and free air temperature, significant additional costs are incurred for the necessary sensors and their installation.

It is an object of this invention to provide a fluid densitometer for incorporation into a fluid speed indicating device.

It is an additional object of this invention to provide a device for measuring fluid density whether the device is stationary or moving with respect to the surrounding air mass.

It is a further object of this invention to incorporate a density correction into a fluid speed indicating device. These objects, and other as will become apparent hereinafter, are accomplished by the present invention.

Basically the present invention is made up of two identical geometry venturis or equivalent venturis which are located at different radii from their center of rotation which produces a steady state pressure between the two venturi pressures. This steady pressure will be a function of the rotational velocity and fluid density. Since the rotational velocity is a known constant, the fluid density can be derived directly from the steady state pressure difference.

BRIEF DESCRIPTION OF THE DRAWINGS

For a fuller understanding of the present invention, reference should now be had to the following detailed description thereof taken in conjunction with the accompanying drawings wherein:

FIG. 1 is a perspective view of the device;

FIG. 2 is a partial sectional view of the device;

FIG. 3 is a sectional view taken along line 3—3 of FIG. 2;

FIG. 4 is a partially cut away perspective view of the section of FIG. 3;

DESCRIPTION OF THE PREFERRED EMBODIMENT

Figure 5:
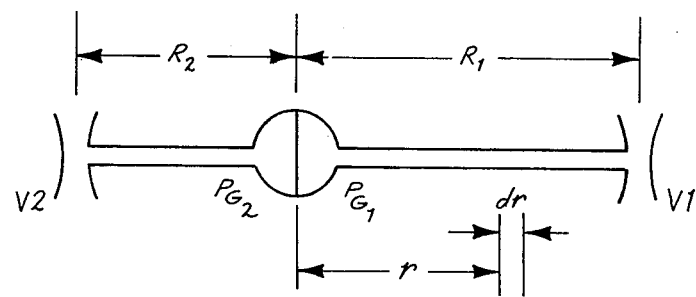
FIG. 5 is a representation of the geometry of the device.

Referring to FIGS. 1–4, the fluid speed sensing instrument and densitometer is generally designated by the numeral 10. Two radially extending and diametrically located bores 14 and 16 extend part way into central hub portion 12. Bores 18 and 20 are perpendicular to and intersect bores 14 and 16, respectively. Cover 22 is sealingly attached to hub portion 12 and together with differential pressure sensing diaphragm and transducer 24 define chambers 26 and 28. A pair of diametrically opposed arms 30 and 40 extend into bores 14 and 16, respectively, of hub portion 12 and are rigidly mounted therein.

Tubular arms 30 and 40 have attached thereto, at different radial distances from hub portion 12, fluid pressure sensing means in the form of venturis 32 and 42, respectively. In addition, in order to have a balanced system, arms 30 and 40 have attached thereto dummy venturis 34 and 44, respectively, which are located at the same radial distances as venturis 42 and 32, respectively. Alternatively, the sensor may take the form of pitot tubes as illustrated in FIG. 1 of U.S. Pat. No. 3,400,584 or any other suitable form of sensing means may be utilized so long as the sensors are asymetrically located. Since the specific type of sensing means forms no part of the present invention, no further description thereof is deemed necessary.

Chamber 26 communicates with venturi 32 via bore 18, port 36 and arm 30. Chamber 28 similarly communicates with venturi 42 via bore 20, port 46 and arm 40. The existence of a difference in pressure between chambers 26 and 28 will cause diaphragm 24 to flex or bend in proportion to the extent of the differential pressure. Mounted in or on diaphragm 24 and forming a part thereof may be any suitable transducer for converting the movement of diaphragm 24 into an electrical signal as, for example, a variable reluctance type pickoff, or simply, a strain gage pickoff.

Hub 12 is mounted for rotation relative to housing 11 and is connected via shaft 50 and gear 52 with gear 53 of driving motor 54 and gear 57 of synchro or resolver 58. The electrical signal output of the transducer is conveyed to the electronic portion of the apparatus by means of slipring and brush assembly 60. The transducer is connected to slipring and brush assembly 60 through hollow shaft 50 by electrical connections (not shown). Since the electronic unit is adequately described in U.S. Pat. No. 3,400,584 and forms no part of the present invention, no further description thereof is necessary.

In operation, the fluid speed indicating apparatus may be mounted on an aircraft to measure the airspeed thereof or it may be used as an anemometer to measure wind velocities or it may be utilized to measure water speed on a ship or submarine. Arms 30 and 40 are driven at a constant speed by driving motor 54 through the gear train. Synchro or resolver 58 provides a phase reference voltage for the transducer output signal. Regardless of the particular application the unit functions as described in U.S. Pat. No. 3,400,584 to sense the cyclic pressure variations at the throats of venturis 32 and 42 due to the alternate movement of arms 30 and 40 into and out of the direction of relative fluid flow. However, since the venturis 32 and 42 are asymetrically located, a fixed pressure variation exists in addition to the cyclic variations and the result is a shifted datum for the cyclic variations.

The result of the shifted datum can best be understood with reference to FIG. 5. The venturis V1 and V2, which correspond to venturis 42 and 32, respectively, of FIGS. 1 and 2, are identical and are located from the center of rotation of the device distances of R1 and R2, respectively. The throats of the venturis V1 and V2 communicate with a cover 22 which is divided by differential pressure sensing diaphragm and transducer 24 into chambers 28 and 26 respectively. Where $p_0$ is the ambient pressure
$\omega R_1$ is the relative velocity of static pressure port with respect to air (remote)
A is the area at the entrance to each venturi
$a$ is the area at the throat of each venturi
$pG_1$ is the gage pressure in chamber 28
$pG_2$ is the gage pressure in chamber 26
$p$ is the density of the air The static pressure at the throat of venturi VI is $$P_{V1} = P_o + \frac{1}{2} \rho \omega^2 R_1^2 - \frac{1}{2} \rho \omega^2 R_1^2 \frac{A^2}{a^2} \quad (I)$$

$$P_{V1} = P_o + \frac{1}{2} \rho \omega^2 R_1^2 \left(1 - \frac{A^2}{a^2}\right)$$

Accounting for the pressure gradient ($dp/dr$) along the tube, for the fluid element $F = ma$ $dp \cdot S = \rho S dr \cdot (+\omega^2 r)$ where $S$ is the cross sectional area of the tube $dp = \rho \omega^2 r dr$ \quad (II)

Assuming $\rho$ is constant along the tube $$\int_{P_{G_1}}^{P_{V1}} dp = \int_0^{R_1} \rho \omega^2 r dr \quad (III)$$

$$P_{V1} - P_{G_1} = \rho \omega^2 \frac{R_1^2}{2}$$

subtracting equation III from equation I $$P_{G_1} = P_o - \frac{1}{2} \rho \omega^2 R_1^2 \frac{A^2}{a^2} \quad (IV)$$

similarly, $$P_{G_2} = P_o - \frac{1}{2} \rho \omega^2 R_2^2 \frac{A^2}{a^2}$$

The transducer senses $p_G - p_G = \Delta p$, the amount of the shifted datum, $$\Delta P = -\frac{1}{2} \rho \omega^2 R_1^2 \frac{A^2}{a^2} + \frac{1}{2} \rho \omega^2 R_2^2 \frac{A^2}{a^2} \quad (V)$$

$$\Delta P = \frac{1}{2} \rho \omega^2 \frac{A^2}{a^2} (R_2^2 - R_1^2)$$

Therefore, in still air, solving equation V for $\rho$ $$\rho = \frac{2a^2 \Delta P}{\omega^2 A^2 (R_2^2 - R_1^2)} \quad (VI)$$

Figure 6:
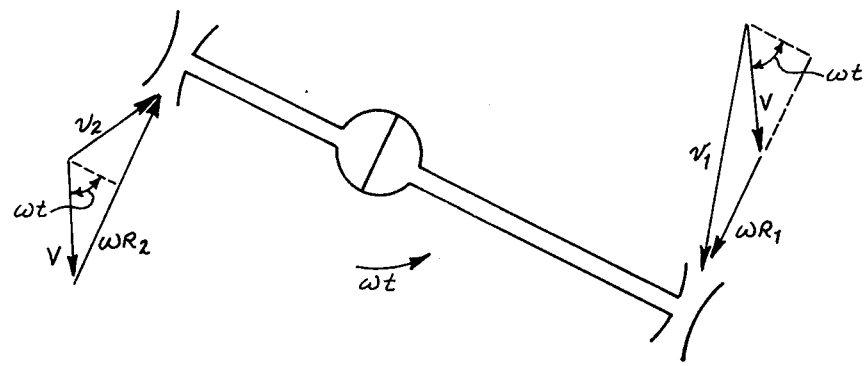
FIG. 6 is a representation of the effects of a translational velocity of the device.

Referring to FIG. 6, with the addition of a translational velocity ($V$) we obtain $v_1^2 = (\omega R_1 + V \sin \omega t)^2 + (V \cos \omega t)^2$ $v_1^2 = \omega^2 R_1^2 + 2 \omega R_1 V \sin \omega t + V^2$ $v_2^2 = (\omega R_2 = V \sin \omega t)^2 + (V \cos \omega t)^2$ $v_2^2 = \omega^2 R_2^2 - 2\omega R_2 V \sin \omega t + V^2$ The corresponding velocities at the venturi throats are $v_{v1}^2 = \frac{A^2}{a^2} (\omega^2 R_1^2 + 2\omega R_1 V \sin \omega t + V^2)$ $v_{v2}^2 = \frac{A^2}{a^2} (\omega^2 R_2^2 - 2\omega R_2 V \sin \omega t + V^2)$ $P_{G_1} = P_o - \frac{1}{2} \rho v_{v1}^2$ $P_{G_2} = P_o - \frac{1}{2} \rho v_{v2}^2$ $P_{G_1} - P_{G_2} = -\frac{1}{2} \rho v_{v1}^2 + \frac{1}{2} \rho v_{v2}^2 = \Delta P$ $\Delta P = \frac{1}{2} \rho \frac{A^2}{a^2} \left[ \begin{array}{c} \omega^2 R_2^2 - 2\omega R_2 V \sin \omega t + V^2 \\ - \omega^2 R_1^2 - 2\omega R_1 V \sin \omega t - V^2 \end{array} \right]$ $\Delta P = \frac{1}{2} \rho \frac{A^2}{a^2} [ \omega^2 (R_2^2 - R_1^2) - 2\omega V \sin \omega t (R_2 - R_1) ]$ If we remove the oscillating terms by low-pass filtering, e.g. an R−C network, we get $$\Delta P = \frac{1}{2} \rho \frac{A^2}{a^2} \omega^2 (R_2^2 - R_1^2)$$

The above equation is the same as equation V. Fluid density can thus be measured by sensing a differential pressure in accordance with equation VI whether the device is stationary or moving with respect to the surrounding air mass.

Strictly speaking, as illustrated and described, venturis 32 and 42 are equivalent venturis since they do not have single throats, but rather, each has a pair of parallel throats due to the presence of arms 30 and 40, respectively. Equivalent venturis represent a manufacturing convenience and operation will be the same as in the case of conventional venturis.

Although a preferred embodiment of the present invention has been illustrated and described, other changes will occur to those skilled in the art. It is therefore intended that the scope of the present invention is to be limited only by the scope of the appended claims.

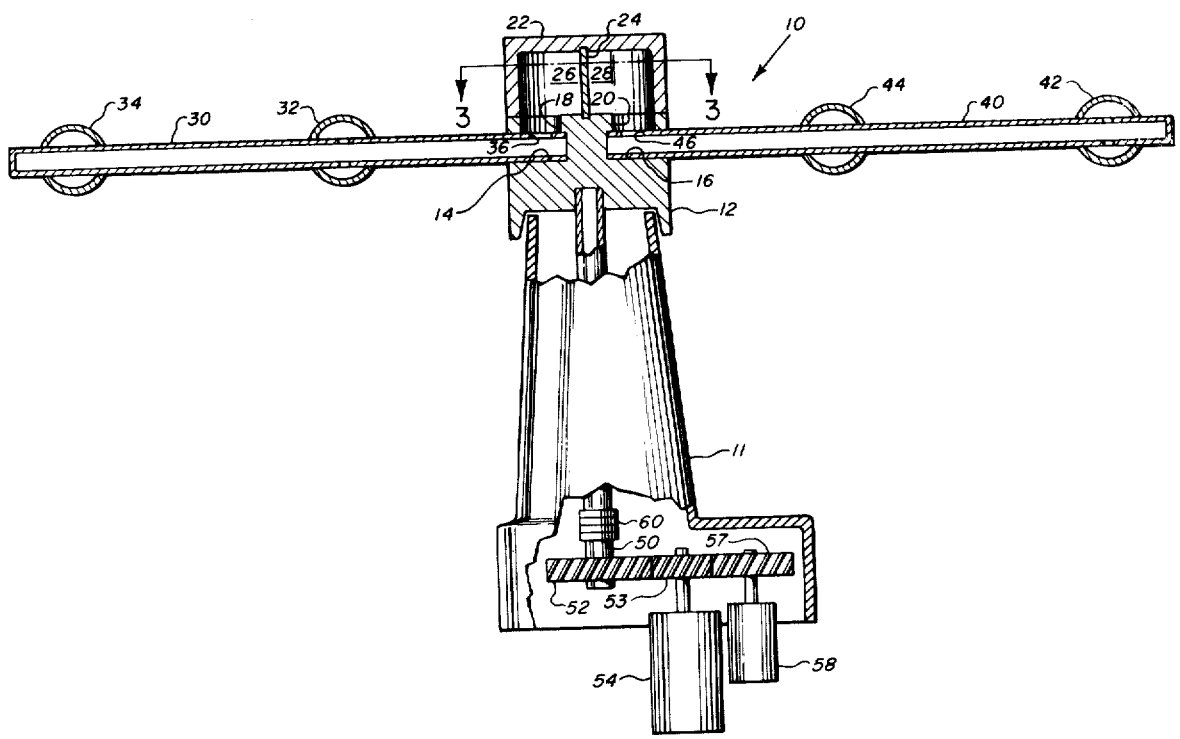

I claim:

1. A fluid speed indicating apparatus and densitometer, comprising:
    A pair of spaced generally coaxially aligned, tubular hollow arms mounted for rotation about an axis intermediate said arms;
    means for rotating said pair of arms at a substantially constant angular speed about said axis;
    two fluid pressure sensing means radially asymmetrically located with respect to said axis and attached to respective arms of said pair of arms; and
    fluid pressure responsive means operatively connected to said two fluid pressure sensing means for sensing the steady state pressure differential between said two fluid pressure sensing means wherein said pressure differential is a function of rotational velocity and fluid density.

2. The fluid speed indicating apparatus and densitometer of claim 1 wherein said two fluid pressure sensing means are venturis.

3. The fluid speed indicating apparatus and densitometer of claim 1 wherein said fluid pressure responsive means includes a transducer unit including a pair of chambers separated by a differential pressure sensing diaphragm.

4. A fluid speed indicating apparatus sensitive to very low fluid speed incorporating a densitometer, comprising:
    two identical geometry fluid pressure sensing means located at substantially different radii from an axis of rotation;
    means for rotating said two fluid pressure sensing means about said axis at a substantially constant angular velocity; and
    fluid pressure responsive means operatively connected to said two fluid pressure sensing means for sensing the steady state pressure differential between said two fluid pressure sensing means wherein said pressure differential is a function of rotational velocity and fluid density.

5. The fluid speed indicating apparatus of claim 4 wherein said fluid pressure responsive means includes a transducer unit including a pair of chambers separated by a differential pressure sensing diaphragm.

* * * * *

UNITED STATES PATENT OFFICE
CERTIFICATE OF CORRECTION

Patent No. 4,065,957　　　　Dated January 3, 1978

Inventor(s) John L. Beilman

It is certified that error appears in the above-identified patent and that said Letters Patent are hereby corrected as shown below:

Cancel the Figure appearing on the title page and substitute the following Figure, as shown on the attached sheet.

Signed and Sealed this

Second Day of May 1978

[SEAL]

Attest:

RUTH C. MASON
Attesting Officer

LUTRELLE F. PARKER
Acting Commissioner of Patents and Trademarks

UNITED STATES PATENT OFFICE
CERTIFICATE OF CORRECTION

PATENT NO. : 4,065,957
DATED : January 3, 1978
INVENTOR(S) : John L. Beilman

It is certified that error appears in the above-identified patent and that said Letters Patent are hereby corrected as shown below: